(12) United States Patent
Koyfman et al.

(10) Patent No.: US 8,568,449 B2
(45) Date of Patent: *Oct. 29, 2013

(54) HIGH STRENGTH SUTURE WITH ABSORBABLE CORE AND SUTURE ANCHOR COMBINATION

(75) Inventors: Ilya Koyfman, Ringoes, NJ (US); Terry E. Lawler, Baldwin, GA (US); Robert C. Di Luccio, Asbury, NJ (US); Dennis D. Jamiolkowski, Long Valley, NJ (US)

(73) Assignee: DePuy Mitek, LLC, Raynham, MA (US)

( * ) Notice: Subject to any disclaimer, the term of this patent is extended or adjusted under 35 U.S.C. 154(b) by 128 days.

This patent is subject to a terminal disclaimer.

(21) Appl. No.: 13/330,741

(22) Filed: Dec. 20, 2011

(65) Prior Publication Data

US 2012/0323273 A1    Dec. 20, 2012

Related U.S. Application Data (60) Division of application No. 12/102,477, filed on Apr. 14, 2008, now Pat. No. 8,109,967, which is a continuation of application No. 10/740,023, filed on Dec. 18, 2003, now Pat. No. 7,357,810.

(51) Int. Cl.
    *A61B 17/04*    (2006.01)
(52) U.S. Cl.
    USPC .......................................... 606/232; 606/228
(58) Field of Classification Search
    USPC .................. 606/144, 148, 154, 228–232, 77; 57/236, 237, 243, 247; 428/373
    See application file for complete search history.

(56) References Cited

U.S. PATENT DOCUMENTS

| | | |
|---|---|---|
| 3,463,158 A | 8/1969 | Schmitt |
| 3,942,532 A | 3/1976 | Hunter |
| 4,105,034 A | 8/1978 | Shalaby |
| 4,455,273 A | 6/1984 | Harpell |
| 4,624,256 A | 11/1986 | Messier |
| 4,632,100 A | 12/1986 | Somers |
| 4,898,156 A | 2/1990 | Gatturna |
| 4,899,743 A | 2/1990 | Nicholson |
| 4,946,468 A | 8/1990 | Li |
| 4,968,315 A | 11/1990 | Gatturna |
| 4,999,074 A | 3/1991 | Afeyan |
| 5,002,550 A | 3/1991 | Li |
| 5,011,473 A | 4/1991 | Gatturna |

(Continued)

FOREIGN PATENT DOCUMENTS

| | | |
|---|---|---|
| DE | 10219860 a1 | 11/2003 |
| EP | 557894 A1 | 9/1993 |

(Continued)

OTHER PUBLICATIONS

EP Search Report dated Mar. 29, 2005 for EP Appl. No. EP 04 25 7953.

(Continued)

*Primary Examiner* — Ryan Severson
*Assistant Examiner* — Katherine M Shi (57) ABSTRACT

A novel high tensile strength semi-absorbable composite suture with minimized non-absorbable mass. The suture has a core made from a bioabsorbable polymer. The core is covered by a braided sheath. The braided sheath is made from an absorbable yarn and a bioabsorbable yarn. The bioabsorbable yarn is made from a least one filament of a bioabsorbable polymer. The nonabsorbable yarn is made from at least one filament of ultra high molecular weight polyethylene.

12 Claims, 10 Drawing Sheets

(56) References Cited

U.S. PATENT DOCUMENTS

| | | |
|---|---|---|
| 5,046,513 A | 9/1991 | Gatturna |
| 5,078,730 A | 1/1992 | Li |
| 5,183,701 A | 2/1993 | Jacobs |
| 5,192,303 A | 3/1993 | Gatturna |
| 5,207,679 A | 5/1993 | Li |
| 5,217,486 A | 6/1993 | Rice |
| 5,261,886 A | 11/1993 | Chesterfield |
| 5,306,289 A | 4/1994 | Kaplan |
| 5,314,446 A | 5/1994 | Hunter |
| 5,358,511 A | 10/1994 | Gatturna |
| 5,456,697 A | 10/1995 | Chesterfield |
| 5,540,718 A | 7/1996 | Bartlett |
| 5,554,171 A | 9/1996 | Gatturna |
| 5,584,836 A | 12/1996 | Ballintyn |
| 5,683,418 A | 11/1997 | Luscombe |
| 5,709,708 A | 1/1998 | Thal |
| 5,782,863 A | 7/1998 | Bartlett |
| 5,782,864 A | 7/1998 | Lizardi |
| 5,814,051 A | 9/1998 | Wenstrom, Jr. |
| 5,961,538 A | 10/1999 | Pedlick |
| 5,980,559 A | 11/1999 | Bonutti |
| 6,045,071 A | 4/2000 | Emsens |
| 6,045,571 A | 4/2000 | Hill |
| 6,264,674 B1 | 7/2001 | Washington |
| 6,270,518 B1 | 8/2001 | Pedlick |
| 6,306,158 B1 | 10/2001 | Bartlett |
| 6,406,479 B1 | 6/2002 | Justin |
| 6,689,153 B1 | 2/2004 | Skiba |
| 6,712,838 B2 | 3/2004 | D'Aversa |
| 6,716,234 B2 | 4/2004 | Grafton |
| 7,329,271 B2 | 2/2008 | Koyfman |
| 7,357,810 B2 | 4/2008 | Koyfman |
| 8,109,967 B2 | 2/2012 | Koyfman |
| 2003/0050666 A1 | 3/2003 | Grafton |
| 2009/0299408 A1 | 12/2009 | Schuldt-Hempe |

FOREIGN PATENT DOCUMENTS

| | | |
|---|---|---|
| EP | 561108 A2 | 9/1993 |
| EP | 1171172 b1 | 1/2001 |
| EP | 1293218 A1 | 3/2003 |
| EP | 1506789 A1 | 2/2005 |
| JP | 49-14800 | 2/1974 |
| JP | 54004493 A | 1/1979 |
| JP | 59130316 A | 7/1984 |
| JP | 63-95060 | 4/1988 |
| JP | 3-80868 | 4/1991 |
| JP | 2002540901 A | 12/2002 |
| JP | 2003339849 A | 12/2003 |
| JP | 2005-177500 | 7/2005 |
| WO | WO 03092758 A1 | 11/2003 |
| WO | WO 2004082466 A2 | 9/2004 |

OTHER PUBLICATIONS

EP Search Report dated May 3, 2005, for European Appln. No. EP 04257893.

Mead et al., "Analysis of Several Ultrahigh Molecular Weight Polyethylene Fibers." ANTEC, Plastics: Plastics Saving Planet Earth, 1997, p. 543, vol. 2; Materials, Society of Plastics Engineers.

HIGH STRENGTH SUTURE WITH ABSORBABLE CORE AND SUTURE ANCHOR COMBINATION

RELATED APPLICATIONS

This application is a divisional of Ser. No. 12/102,477, filed on Apr. 14, 2008 which is a continuation of application Ser. No. 10/740,023, filed on Dec. 18, 2003. The complete disclosures of the aforementioned related U.S. patent applications are hereby incorporated herein by reference for all purposes.

TECHNICAL FIELD

The field of art to which this invention relates is surgical sutures, in particular, surgical sutures having both bioabsorbable and nonabsorbable components.

BACKGROUND OF THE INVENTION

Surgical sutures are well known medical devices in the art. The sutures may have braided or monofilament constructions, and may be provided in single-armed or double-armed configurations with a surgical needle mounted to one or both ends of the suture, or may be provided without surgical needles mounted. The sutures are used in a variety of conventional medical and surgical procedures to approximate tissue, affix or attach implants to tissue, etc. Surgical sutures may be made from a variety of known bioabsorbable and nonabsorbable materials. For example, sutures are known to be made from aromatic polyesters such as polyethylene terephthalate, nylons such as nylon 6 and nylon 66, polyolefins such as polypropylene, silk, and other nonabsorbable polymers. In addition, sutures may be made from polymers and copolymers of p-dioxanone (also known as 1,4-dioxane-2-one), ε-caprolactone, glycolide, L(−)-lactide, D(+)-lactide, meso-lactide, trimethylene carbonate, and combinations thereof. Of particular utility is polydioxanone homopolymer.

Surgical sutures are typically available in a range of conventional sizes for a variety of conventional surgical procedures. The size of the suture used by the surgeon for any particular procedure is dictated in part by the type of tissue to be sutured, the relative size of the tissue structure, as well as the forces that will be applied to the sutures by the approximated tissue after the surgical procedure has been completed. Similarly, the type of suture selected will be dictated by the procedure. Nonabsorbable sutures are typically used for applications such as cardiovascular, vascular, orthopedic, gastrointestinal and the like wherein a nonabsorbable suture is desired or required because a permanent or an extended period of fixation is required during the healing period, e.g., implantation of a heart valve prostheses. Bioabsorbable sutures are typically used for applications such as plastic surgery, skin fixation and certain soft tissue approximation, and the like. A bioabsorbable suture may be used when extended tissue approximation or fixation is not required as long as the suture maintains adequate strength during the healing period, and it is desirable to replace the suture with autologous tissue such as skin or soft tissue during the healing process.

In certain applications where significant tensile forces will be applied on a suture, it is desirable to use materials that will provide high tensile strength with minimal suture size or cross-section. The tensile strength of a suture is known to be a function of several parameters including material, suture size, filament diameter, type of construction (i.e., braided versus monofilament), ratio of sheath to core in a braided construction, type of material in the core, etc. In particular it is known to use ultra high molecular weight polyethylene (hereinafter referred to as UHMWPE) to construct sutures. Sutures made from ultra high molecular polyethylene have the advantage of having high tensile strength while having a smaller suture size. A disadvantage of such sutures is that ultra high molecular weight polyethylene is a relatively slippery material. This inherent slipperiness may affect the knot integrity of a suture. In a typical surgical procedure, after the surgeon makes multiple passes of the suture through tissue so that it is properly approximated and stitched, one or more conventional knots are placed in the suture by the surgeon to maintain the suture in place and thereby prevent it from loosening. Loosening of a suture may allow the approximated tissue to split apart, thereby compromising the surgical procedure and preventing healing with the potential for causing catastrophic effects (e.g., anasotomosis graft blow out in cardiovascular repairs, implant dislodgement, organ failure, soft tissue dislocation from a bone, etc.).

In order to improve the knot holding characteristics (e.g., knot strength) of ultra high molecular polyethylene sutures, it is known to combine the ultra high molecular weight polyethylene yarn component with another yarn component that has surface friction higher that the ultra high molecular weight yarn component. For example it is known to provide a ultra high molecular weight polyethylene suture having an nonabsorbable core, an ultra high molecular weight polyethylene core or an aromatic polyester core with an outer sheath surrounding the core braided from a combination of ultra high molecular weight polyethylene fiber yarns and yarns made from fibers of a nonabsorbable material such as an aromatic polyester. It is also known to have a suture that has a nonabsorbable ultra high molecular weight polyethylene core or an aromatic polyester core surrounded by an outer braided sheath braided from a yarn made from ultra high molecular weight polyethylene fibers and a yarn made from fibers of a bioabsorbable polymer.

Although such composite ultra high molecular weight polyethylene sutures provide increased tensile strength, there are several disadvantages associated with their use. One disadvantage is the possibly diminished knot characteristics that they provide. Typically such sutures produce a large knot having increased mass, size and/or volume. A knot in a nonabsorbable suture remains in the patient's body after the tissue has been approximated and the healing has been completed, and may irritate soft tissue and cause patient discomfort and pain. It is known that from a medical perspective it is desirable to minimize the mass of an implant in tissue. In addition, it is advantageous for an implant to allow for autologous tissue migration or in-growth to provide for better healing. A bioabsorbable implant such as an absorbable suture permits tissue ingrowth as the mass of the implant is resorbed or degraded by the patient's body to provide for better healing. This healing process allows the patient's tissue to assume the tissue loads as the absorbable portion of the implant or suture resorbs/degrades and loses structural integrity and strength. The ultra high molecular weight polyethylene sutures of the prior art have a dense nonabsorbable volume and knot mass, even when combined with a bioabsorbable component, which for the most part remains behind after the tissue healing process has occurred, contributing to problems discussed above.

Accordingly, what is needed in this art are novel composite sutures constructed from materials providing high tensile strength, and bioabsorbable materials, wherein the composite sutures provide optimal tensile strength with minimal mass of high tensile strength material, and have good knot strength and knot security, and reduced in vivo knot profile over time, while allowing tissue ingrowth.

SUMMARY OF THE INVENTION

Therefore novel surgical sutures are disclosed. The sutures have a core of yarn made from filaments of a bioabsorbable polymer. The core is surrounded by a sheath braided from a yarn made from filaments of ultra high molecular weight polyethylene and a yarn made from bioabsorbable polymer fibers.

Yet another aspect of the present invention is a surgical suture. The surgical suture has a core and a braided sheath surrounding the core. The core is made from a yarn made from filaments of a bioabsorbable polymer. The sheath is braided from a yarn made from ultra high molecular weight polyethylene fibers and a yarn made from bioabsorbable polymer fibers. The bioabsorbable core and the bioabsorbable fibers include one or more active agents including pharmaceuticals, bioceramics, and anti-microbials.

Still yet another aspect of the present invention is a method of approximating tissue. A surgical suture is provided. The surgical suture consists of a core and a braided outer sheath surrounding the core. The core consists of at least one yarn made from filaments of a bioabsorbable polymer. The sheath is braided from at least one yarn made from ultra high molecular weight polyethylene filaments and at least one yarn made from bioabsorbable polymer filaments. The suture is stitched into a tissue to approximate the tissue and at least one surgical knot is optionally applied to the suture.

Still yet another aspect of the present invention is a method of improving absorption profile of the absorbable component of the suture.

Yet another aspect of the present invention is a method of reducing the knot profile of a knot in a surgical suture. A surgical suture is provided. The surgical suture consists of a core and a braided outer sheath surrounding the core. The core consists of at least one yarn made from filaments of a bioabsorbable polymer. The sheath is braided from at least one yarn made from filaments of ultra high molecular weight polyethylene and at least one yarn made from bioabsorbable polymer filaments. The suture is stitched into a tissue to approximate the tissue. A surgical knot is made in the suture to secure the suture. The knot has a knot profile that is reduced as the bioabsorbable component is absorbed or degraded in vivo over time.

A further aspect of the present invention is a method of providing the release of active components including pharmaceuticals, and antimicrobials through coatings applied to said sutures.

Yet another aspect of the present invention is a combination of a suture anchor and the above-described surgical suture. The suture anchor has an anchor body and a suture mounting opening. The suture is mounted to the suture mounting opening.

Still yet a further aspect of the present invention is a method of affixing soft tissue to the surface of a bone using the suture anchor and suture combination of the present invention. The anchor is mounted in bone, and the suture is used to affix the soft tissue to the surface of the bone.

These and other aspects and advantages of the present invention will become more apparent by the following description and accompanying drawings.

DISCLOSURE OF PREFERRED EMBODIMENT

The ultra high molecular weight polyethylene used to manufacture the sutures of the present invention will typically have a weight average molecular weight of about 500,000 g/mole to about 5,000,000 g/mole, more typically about 1,000,000 g/mole to about 3,000,000 g/mole, and preferably about 2,000,000 g/mole to about 2,500,000 g/mole. The ultra high molecular weight polyethylene typically has a tenacity of about 20 cN/dtex to about 40 cN/dtex, more typically about 27.5 cN/dtex to about 38.7 cN/dtex.

The ultra high molecular weight polyethylene will preferably be in the form of a conventional yarn having multiple filaments. Such yarns are commercially available for use in the manufacture of medical devices such as surgical sutures. For example, an ultra high molecular weight polyethylene yarn useful in the sutures of the present invention is 110 dtex Dyneema Purity yarn available from DSM, Netherlands.

The bioabsorbable polymers useful to manufacture the sutures of the present invention include conventional bioabsorbable and biodegradable polymers and copolymers. Of particular utility are the synthetic bioabsorbable polymers prepared from lactone monomers selected from the group consisting of p-dioxanone (also known as 1,4-dioxane-2-one), ε-caprolactone, glycolide, L(-)-lactide, D(+)-lactide, meso-lactide, trimethylene carbonate, and combinations thereof. These polymers include polyglycolide, poly(caprolactone-co-glycolide), poly(glycolide-co-lactide), polylactide, polycaprolactone and the like and equivalents thereof; advantageously the bioabsorbable polymer is polydioxanone homopolymer. The term "bioabsorbable" as used herein is defined to mean both bioabsorbable and biodegradable. It is particularly preferred to use a polydioxanone polymer for the bioabsorbable component of the sutures of the present invention. The bioabsorbable component of the sutures will preferably consist of a yarn containing multiple filaments made from the bioabsorbable polymer. Methods of manufacturing such yarns are known in this art. If desired, although not preferred, the bioabsorbable yarn component may be made of filaments of more than one bioabsorbable polymer and/or copolymer.

The ultra high molecular weight polyethylene composite sutures of the present invention will typically contain about 40 wt. % to about 70 wt. % of bioabsorbable polymer, more typically about 50 wt. % to about 65 wt. % of bioabsorbable polymer, and preferably about 52 wt. % to about 62 wt. % of bioabsorbable polymer, and more preferably about 62 wt. % of bioabsorbable polymer. For example, the braided sheath may consist of 45 wt. % ultra high molecular weight polyethylene and 55 wt. % of polydioxanone, while the core is 100 wt. % polydioxanone, yielding a suture of the present invention consisting of about 38 wt. % ultra high molecular weight polyethylene and 62 wt. % of polydioxanone.

The composite ultra high molecular weight polyethylene sutures of the present invention may have a standard range of conventional suture sizes ranging from but not limited to USP standard sizes 9/0 to 5. The selection of a particular suture size by the surgeon will depend upon several factors including type of tissue, size of the wound being approximated, tissue load, post operative stresses on the suture, location of the suture, the type of surgical procedure, etc.

The bioabsorbable component of the sutures of the present invention may include various active agents. The active agents that may be added to the bioabsorbable component of the sutures of the present invention include a variety of pharmaceutical compositions and bone-inducing compositions, as well as biologics and bio-active materials. The active agents include, but are not limited to, known anti-inflammatories, anti-infectives, and analgesics or pain killers. Examples of specific pharmaceutical compounds include inderal, diclofenac, fenoprofen, ketoprofen, ketorolac, naproxen, bupivicaine, lidocaine, mepivicaine. Examples of antimicrobials include triclosan and chlorhexidine digluconate. The bone inducing compositions may include known materials such as tricalcium phosphate, bioceramics, bioglasses, calcium hydroxy apatite, combinations thereof and the like. If desired, the coatings used for the sutures of the present invention may contain such active agents The amount of such active agents included in the bioabsorbable component of the sutures of the present invention will be sufficient to provide a therapeutically effective dose. Similarly, the amount of active agent used in a coating will be sufficient to provide a therapeutically effective dose.

The sutures of the present invention will typically be braided from conventional fiber-containing yarns using conventional braiding equipment. Processes and methods for manufacturing surgical sutures are known in this art and are disclosed, for example, in U.S. Pat. Nos. 5,314,446 and 6,045,071, both of which are incorporated by reference. In addition to braiding, sutures typically require one or more additional conventional process steps after braiding including but not limited to hot stretching, scouring, annealing, coating, tipping, cutting, needle, attachment, packaging and sterilization.

Hot stretch is needed for reducing braid diameter and heat setting the yarns in the braid to prevent so-called "brooming", when braid edge would open up or unravel after cutting. The scouring process is required for removal of spin finishes that are applied to the yarns during extrusion. Annealing is required to remove residual monomer and for increasing crystallinity. One purpose of a coatings is to provide good suture slidability without unduly compromising knot security. Tipping is optionally needed for a good needle attachment, depending upon the suture. In addition to spin finish removal, the scouring process also helps in removing dust particles and oil droplets that may be deposited during braiding. At the same time, the scouring agent should not have significant adverse effects on suture properties.

It is also known that, in general, coating provides good suture slidability, e.g., through tissue. Coatings may provide the lubricity necessary to achieve smooth tiedown and knot slide performance. While this lubricity is required for smooth tiedown, the coating level(s) must be precisely controlled in order to maintain knot security.

After a suture is optionally tipped in a conventional manner and cut to length, needle attachment takes place. Then, the needle/suture combinations are packaged, and finally sterilized, for example with an Ethylene Oxide process, or other conventional sterilization processes depending on the type of material and packaging, e.g., gamma radiation, autoclaving, plasma, etc.

Figure 1A:
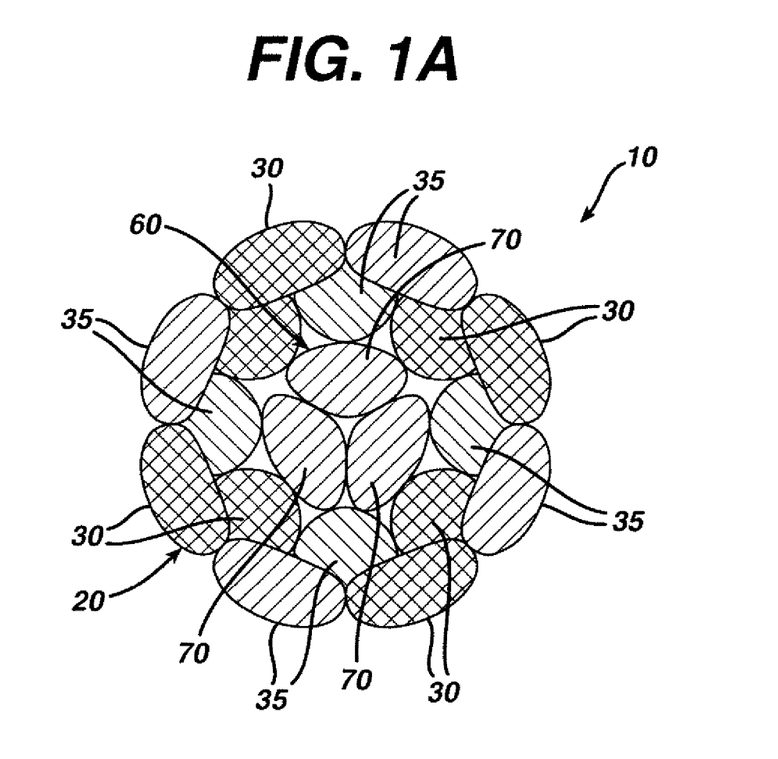
FIG. 1A illustrates a cross-section of a preferred embodiment of a suture of the present invention.
Figure 1B:
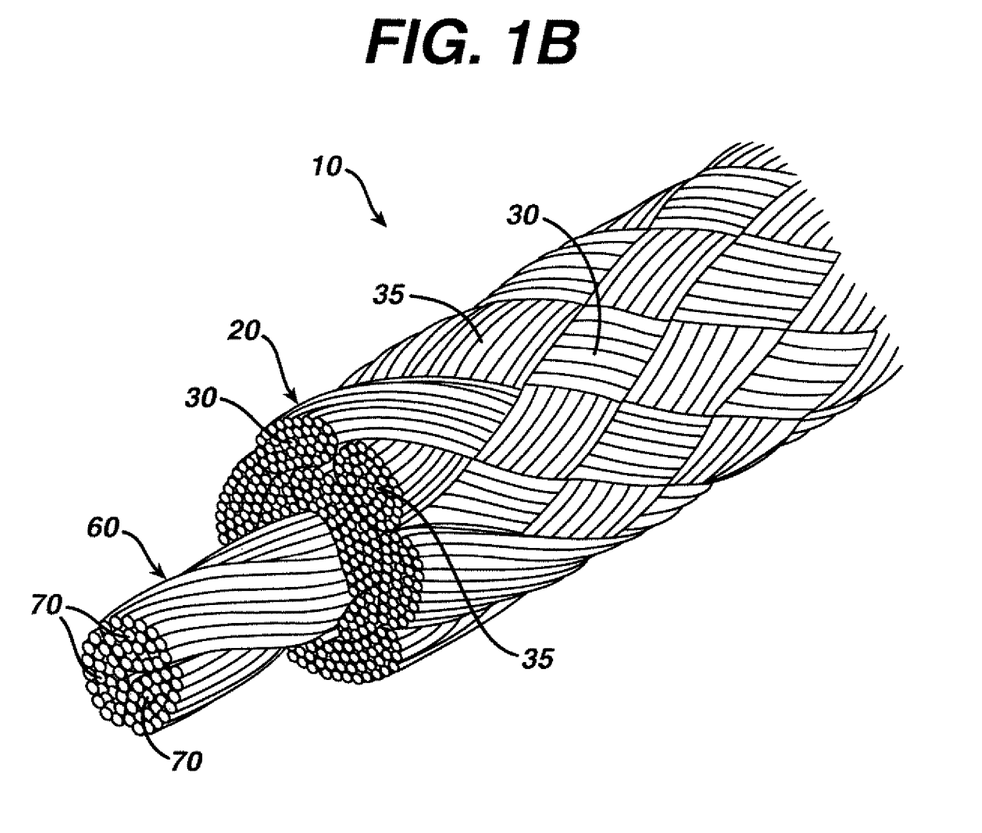
FIG. 1B illustrates an exploded perspective view of the suture of FIG. 1A.

Referring to FIG. 1, a cross-section of a preferred embodiment of a suture of the present invention is seen. The suture 10 is seen to have an outer sheath 20 and an inner core 60. The sheath 20 is seen to be a braided structure of two yarns in intertwining contact. Yarn 30 is composed of filaments of ultra high molecular weight polyethylene. Yarn 35 is composed of filaments of a bioabsorbable polymer such as polydioxanone. The core 60 is seen to have yarns 70 composed of bioabsorbable polymer fibers. The yarns 70 are preferably made of the same bioabsorbable polymer as yarn 35, but alternate embodiments may be made from a different bioabsorbable polymer.

Figure 2A:
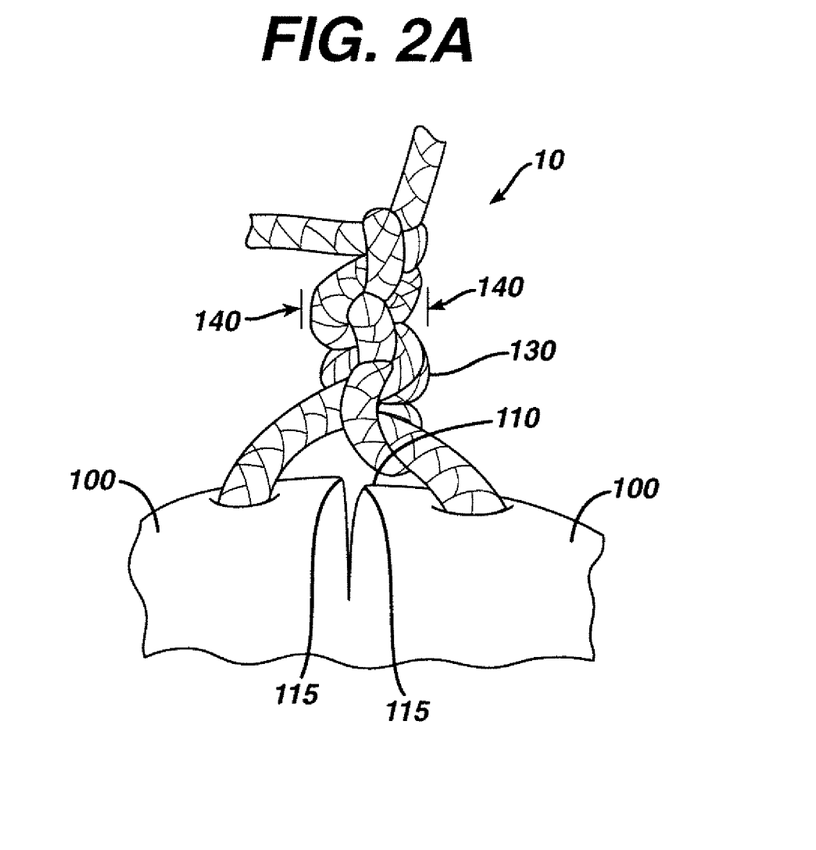
FIG. 2A illustrates a profile of a knot tied into a suture of the present invention, after the surgeon has emplaced the suture in tissue to approximate the tissue by stitching.
Figure 2B:
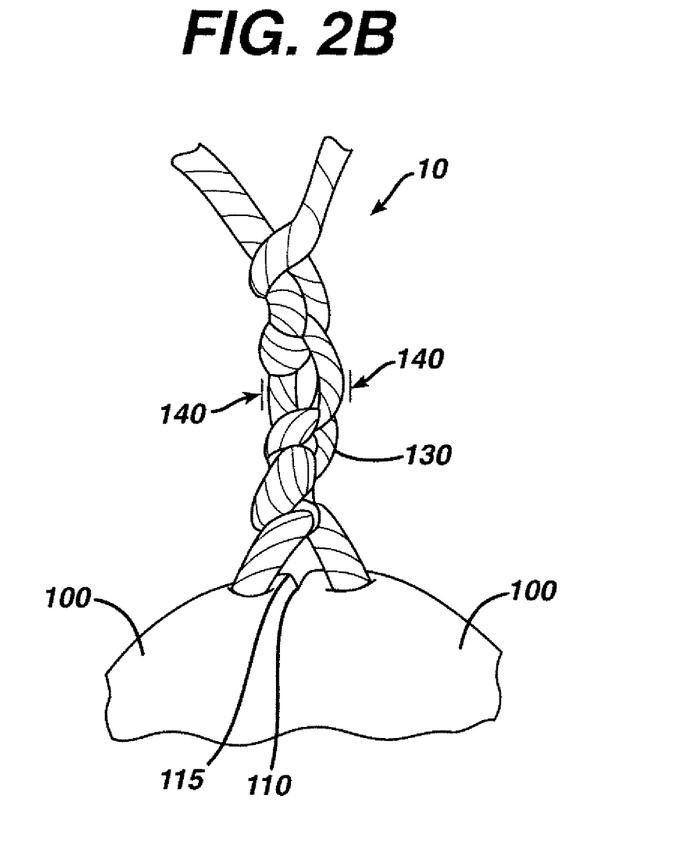
FIG. 2B illustrates the knot of FIG. 2A after the bioabsorbable component has been absorbed, and the knot profile has been reduced.

When used in a surgical procedure, the sutures of the present invention are typically knotted, ultimately, by the surgeon after stitches have been made in tissue to emplace the suture, in order to secure the suture. The surgical knots that are utilized for this purpose are well known to surgeons and medical practitioners and include the following types of knots: surgeon's throw, Revo knot, SNC knot, Tennessee Slider, Modified Roeder, square knot, half-hitch and reverse half-hitch, Duncan loop, etc. As seen in FIG. 2A, a suture 10 of the present invention is seen to have been emplaced in tissue 100 to secure and approximate the edges 115 of a wound 110. A half-hitch and reverse half-hitch knot 130 has been tied in the suture 10 to secure stitches in place. The knot 130 is seen to have a knot profile characteristic 140. The term knot profile characteristic is defined to mean the overall mass and volume of a suture knot including a spatial shape or configuration. The term knot profile dimension is defined to mean an overall thickness of the knot, for example, when the knot is tied, the ears of the knot will usually be lying parallel to the plane of the approximated tissue. The knot 130 seen in FIG. 2A has the knot profile characteristic 140 immediately after implantation. The suture 10 of FIG. 2A is illustrated in FIG. 2B, in vivo, after a sufficiently long period of time has passed to effectively provide for absorption of the bioabsorbable components. The knot 130 is seen to have a reduced knot profile characteristic 140 attributable to the loss of mass and volume of the absorbable component. Surprisingly and unexpectedly, the strength of the knot 130 is not significantly reduced, even though the absorbable component of suture 10 has been absorbed away from the suture 10. In addition, tissue in-growth is seen to have occurred.

Figure 3A:
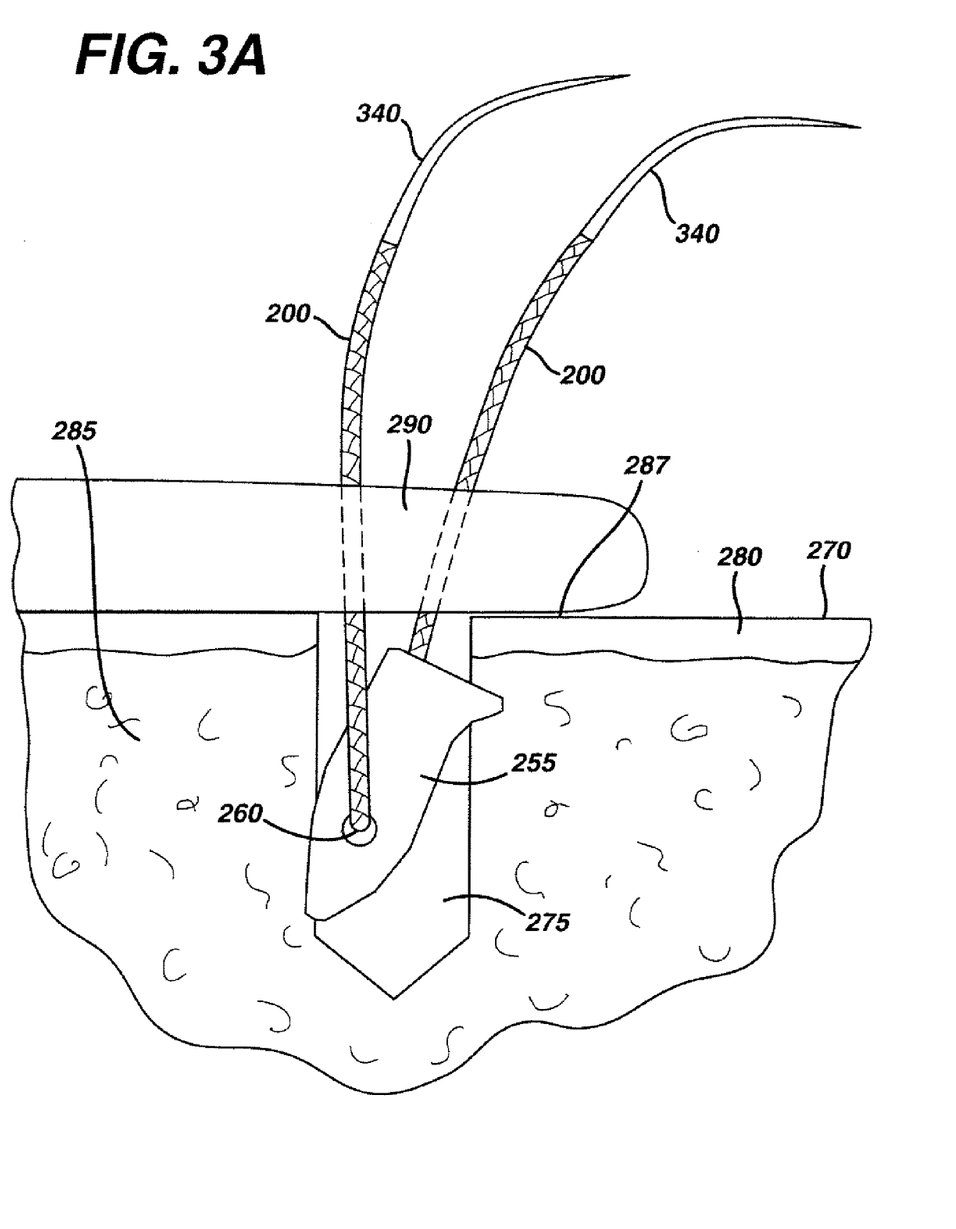
FIG. 3A illustrates the suture of the present invention mounted to a suture anchor implanted in a bone, wherein the suture secures soft tissue to the surface of the bone, prior to the surgical needles being cut off from the ends of the suture.
Figure 3B:
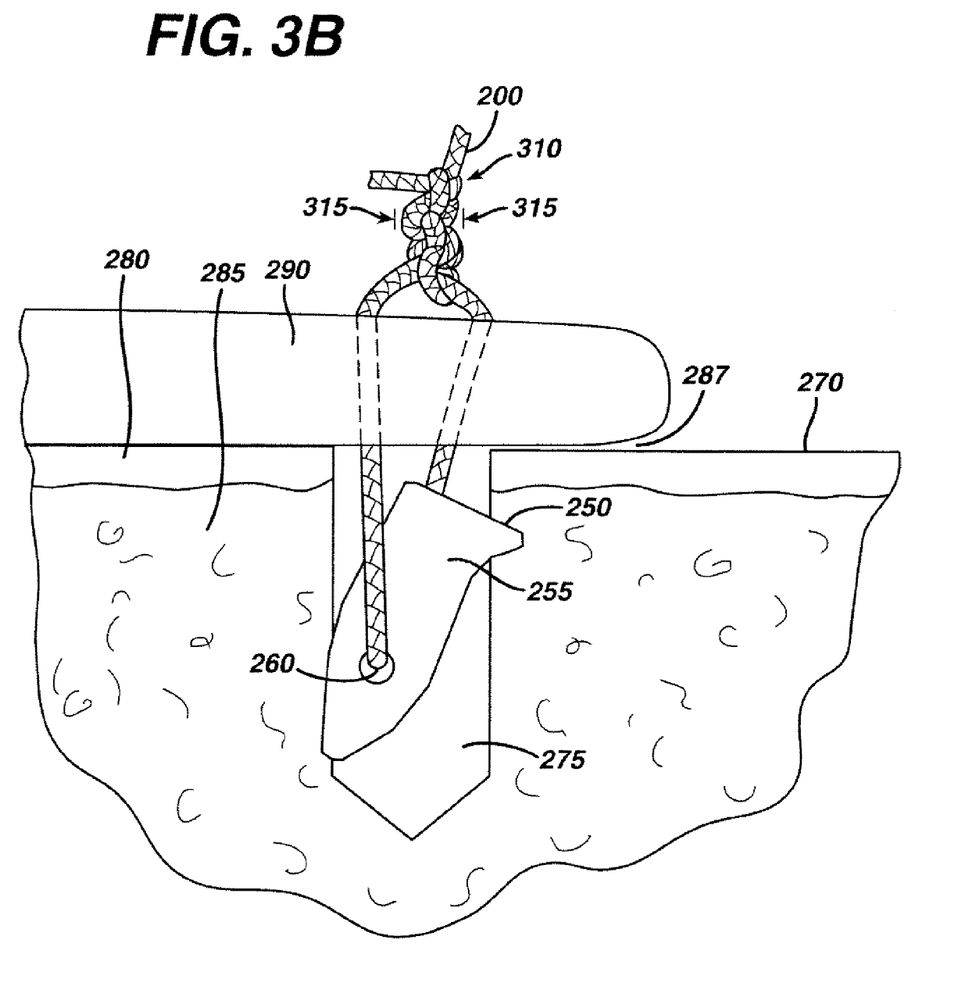
FIG. 3B illustrates the suture and suture anchor of FIG. 3A after the needles have been cut from the suture and a surgical knot has been made in the suture.

The sutures of the present invention are preferably used in conjunction with suture anchors to repair soft tissue injuries. Suture anchors and procedures using suture anchors are disclosed in the following United States patents which are incorporated by reference: U.S. Pat. Nos. 4,632,100, 4,999,074, 5,814,051, 5,709,708, 5,782,864, 6,270,518, 5,540,718, 6,264,674, 6,270,518, 6,306,158, 5,961,538, 5,782,863, 5,683,418, 5,554,171, 5,078,730, 4,632,100, 5,217,486, 5,011,473, 4,898,156, 4,899,743, 4,946,468, 4,968,315, 5,002,550, 5,046,513, 5,192,303, 5,207,679, 5,358,511. As seen in FIGS. 3A and 3B, a suture 200 of the present invention is mounted to a conventional bioabsorbable suture anchor 250. Anchor 250 is seen to have anchor body 255. The suture 200 is mounted through suture mounting passage 260 in anchor body 255. The anchor 250 is seen to be mounted in a bore hole 275 drilled into a bone 270. The anchor 250 is mounted in the cancellous portion 280 of the bone 270 below the cortex 285 and engages cancellous portion 280. Soft tissue 290 is seen to be approximated to bone surface 287 by suture 200. Suture 200 is seen to have conventional surgical needles 340 mounted to each end 210. The tissue is secured by placing a half-hitch and reverse half-hitch knot 310 in suture 10. The knot 310 is seen to have knot profile characteristic 315. Surgical needles 340 are cut from suture 200 prior to the completion of the procedure.

It is also known to those skilled in the art that polydioxanone absorbable yarns with a relatively small filament diameter (about 3 denier per filament or smaller) will lose strength faster than yarns of the same total denier that have filaments with substantially larger denier per filament (e.g. 12 denier per filament). In many surgical indications, substantial strength needs to be maintained during the critical wound healing process. There is thus a need to use larger diameter polydioxanone filaments—higher denier per filament yarns. On the other hand, it is a well-known principle that column strength and bending strength of cylinders are both very dependent on diameter. It is thus surprising and unexpected that the bi-component suture that is made with larger diameter 12 denier per filament (dpf) yarn does not become stiffer and still retains desirable handling characteristics similar to the suture made with the much smaller filament diameter yarns (3 dpf).

The following examples are illustrative of the principles and practice of the present invention, although not limited thereto.

Example 1

A suture of the present invention was manufactured in the following manner. The suture was made using a conventional maple (hollow) braider. The composite suture had a sheath of ultra high molecular weight polyethylene yarn and polydioxanone yarn. The sheath contained 45 wt. % ultra high molecular weight polyethylene and 55 wt. % polydioxanone. The core of the suture consisted of 100 wt. % polydioxanone yarn. Overall, the suture consisted of 38 wt. % ultra high molecular weight polyethylene and 62 wt. % polydioxanone. The non-absorbable component of the suture construction consisted of eight 100-denier Dyneema Purity ultra high molecular weight polyethylene multifilament yarns (manufactured by DSM) that were loaded on the braider in the counterclockwise direction, and the polydioxanone component was a conventional multifilament polydioxanone yarn, such as that used to manufacture polydioxanone sutures by Ethicon, Inc., Somerville, N.J. The polydioxanone component consisted of eight polydioxanone 60×2 denier dyed multifilament yarns that were loaded on the braider in the clockwise direction. The braid had a core construction that consisted of dyed polydioxanone 60×⅔ multifilament yarns. Pick count is selected at around 47-48 ppi. The absorbable core was selected to minimize suture mass in the body after absorption and provide better suture cutting ability. The braid construction is described in the Table 1.

TABLE 1

| Material | Braider Carriers | Clockwise Direction | Counter Clockwise Direction | Pick Count | Core Construction |
|---|---|---|---|---|---|
| Dyneema yarn Polydioxanone yarn | 16 | Polydioxanone yarn 60 × 2/8 | Dyneema yarn 100 × 1/8 | 46 | Polydioxanone yarn 60 × 2/3 |

The off-braider material required additional conventional processing in order to become a suitable suture material. The process flow can be described as follows: hot stretching, annealing, scouring, coating, tipping, and cutting.

The suture was hot stretched at 90° C., which is 5 degrees above the annealing temperature. Such arrangement is needed in order to maintain the heat set memory acquired by braid during the hot stretch. Due to a very low elongation of Dyneema yarn (about 4%), the percentage stretch was set at 8%. Such relatively low percentage of stretch does not damage the braid, and at the same time provides a sufficient force for consolidating the braid structure.

The material was wound onto the racks, and scoured for about 80 min in acetone. Spin finish residuals were reduced to acceptable levels.

The material was coated with a conventional absorbable coating with a concentration level of 4.5% (wt./wt.) of a 90/10 copolymer of caprolactone/glycolide dissolved in ethyl acetate using a drip process. The suture's unique absorbable/non-absorbable construction has led to the evaluation of both absorbable and non-absorbable coatings.

In certain surgical circumstances, it may be preferred that the coating absorbs prior to the absorption of the polydioxanone component of the suture.

Since polydioxanone (hereinafter referred to as PDS) material is susceptible to UV light and exposure to ambient air in general, the exposure time limits have to be maintained during suture processing.

Example 2

The tensile strength of the suture of Example 1 was tested in accordance with the United States Pharmocopoeia using the method for a constant rate of extension. In addition, the tensile strengths of the following commercially available sutures were also determined: an aromatic polyester (hereinafter referred to as PET) suture such as one manufactured by Ethicon, Inc., Somerville, N.J., and an ultra high molecular weight polyethylene/PET suture such as FIBERWIRE manufactured by Arthrex, Inc., Naples, Fla. The results of the testing are presented in Table 2.

This example compared straight and knot tensile strength of suture of the present invention to the FiberWire suture and the PET suture. The comparison shows that the use of polydioxanone in the core of the suture of the present invention had no adverse effect upon the physical properties of the suture. In order to compare strength of the sutures that have slightly different diameters, straight and knot strength was normalized to the cross-sectional area of the suture and expressed in Kpsi.

TABLE 2

| Braid I.D. | Diameter (mils) | Straight Tensile (lbs) | Straight Tensile (Kpsi) | Elongation % | Knot (lbs) | Knot (Kpsi) |
|---|---|---|---|---|---|---|
| 1 Present Invention | 22.87 | 63.81 | 155.63 | 13 | 29.50 | 71.95 |
| 2 UHMWPE/ PET | 21.89 | 51.61 | 137.19 | 8 | 26.74 | 71.08 |
| 3 PET | 21.29 | 31.34 | 87.06 | 22 | 15.10 | 41.94 |

The test results showed the suture of the present invention had equivalent or superior tensile strength, and knot break tensile strength than the ultra high molecular weight polyethylene/an aromatic polyester nonabsorbable suture and the an aromatic polyester suture.

Example 3

In Vitro Knot Tensile Breaking Strength Retention (BSR) & Mass Loss Over Time

Samples of the suture of Example 1 for In Vitro Knot Security were degraded in a buffer of pH 7.27 and a water bath with temperature 57° C. Knots were secured with 5 throws and placed in the buffer container. Five knot-secured sutures from each lot were tested for each time period. Sutures were tested before and after degradation using the Instron Tensile Tester employing a Hermann's loop fixture, 2"/min XH speed to obtain breaking strength. Note: Because this test was a loop, the knot strength was approximately twice that for the typical USP knot tensile test. The mass remaining was obtained by drying and weighing the sutures after different times in the buffer solution.

Figure 4:
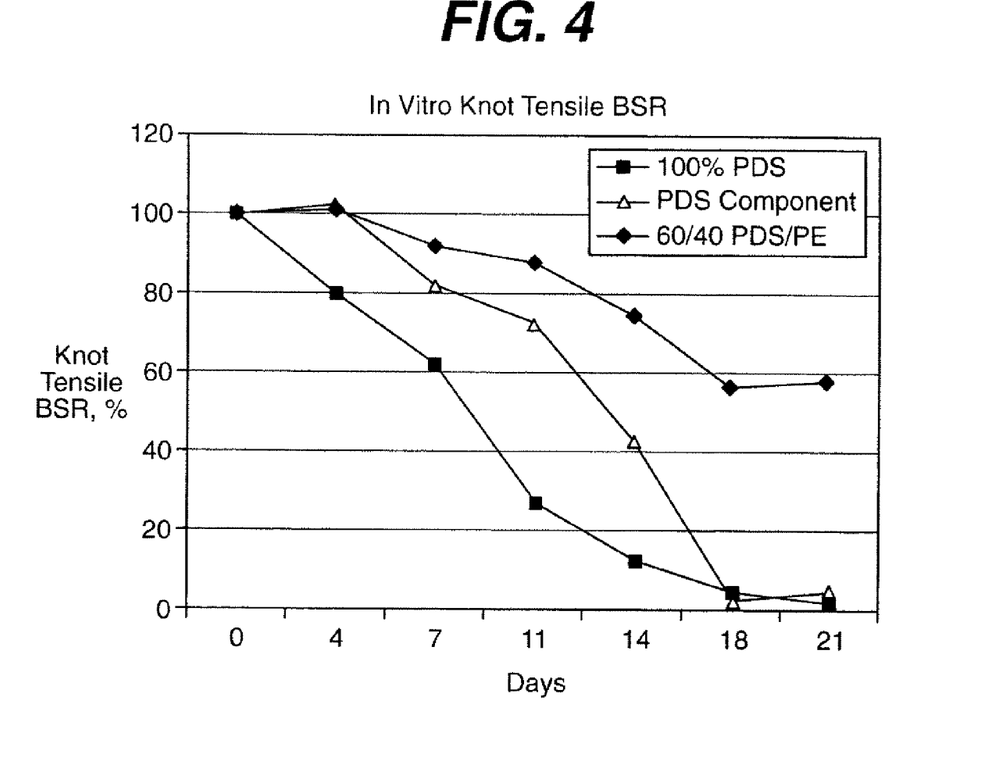
FIG. 4 is a graph of In Vitro Knot Tensile BSR % vs. Days presenting data of Example 4

In addition to the suture of Example 1 consisting of about 40 wt. % high molecular weight polyethylene and about 60% polydioxanone, another suture was tested consisting of 100 wt % polydioxanone. Table 3 provides the in vitro knot strength results versus days in the buffer. The 60/40 polydioxanone/ultra high molecular weight polyethylene suture reached approximately 30 lb strength after 18 days and was relatively constant thereafter. By design the ultra high molecular weight polyethylene strength after loss of the polydioxanone was intended to be approximately 30 lb to match the strength of nonabsorbable an aromatic polyester sutures. Thus, the strength retention of the polydioxanone component of the polydioxanone/ultra high molecular weight polyethylene suture was estimated by subtracting 30 lb from the strength for the suture. This data was also used to present the data as a percent remaining in Table 3 and graphically in FIG. 4.

It was not anticipated that the polydioxanone in the polydioxanone/polyethylene suture would maintain higher strength over time than for a 100% polydioxanone braided suture.

Figure 5:
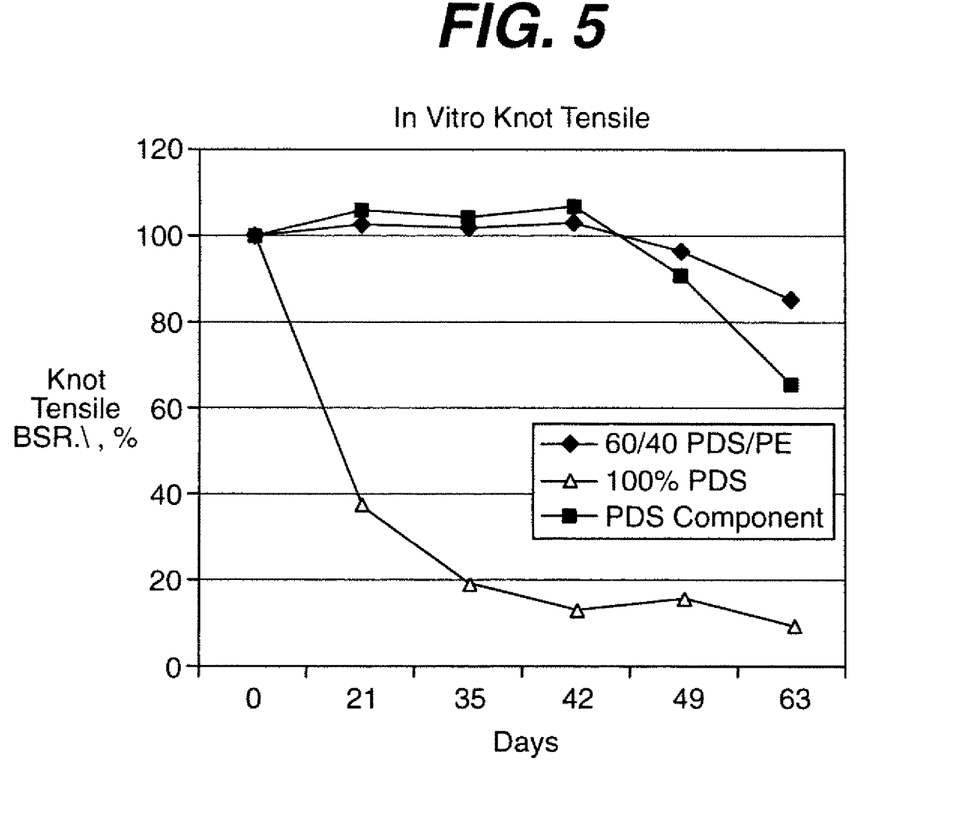
FIG. 5 is a graph of In Vivo Knot Tensile BSR % vs. Days presenting data of Example 4.

In Table 4 and FIG. 5, the weight remaining for the knotted suture is presented. The calculation for percent weight remaining for the polydioxanone component of the bicomponent suture was based on the fact that the suture design was 40 wt. % high molecular weight polyethylene and 60 wt. % polydioxanone. So the wt. % remaining for the polydioxanone component is obtained by subtracting 40 percent from the bi-component suture and dividing by 0.60.

Note that the weight loss for the polydioxanone component of the bicomponent suture was not atypical of that obtained for the 100% polydioxanone suture. Thus it becomes even more surprising that the knot strength retention in the polydioxanone component of the bicomponent suture remains higher than expected while the mass loss is as expected. This feature is highly desired to maintain good strength yet decrease mass.

TABLE 4

In Vitro Mass Loss

| Days | 100% PDS | 60/40 PDS/PE | PDS Component* |
|---|---|---|---|
| 0 | 100 | 100 | 100 |
| 4 | 100 | 100 | 100 |
| 7 | 101 | 102 | 103 |
| 11 | 99 | 102 | 103 |
| 14 | 95 | 98 | 97 |
| 18 | 84 | 89 | 82 |
| 21 | 79 | 81 | 68 |
| 30 | 26 | 48 | 13 |

*Based on subtracting the 40% by weight for the UHMW PE component and divide by 60% which was the starting content of the PDS.

Example 4

In Vivo Knot Tensile Breaking Strength Retention (BSR)

In vivo breaking strength retention was conducted for the suture of Example 1 in the following manner.

The method used for in vivo knot tensile was the same as for the in vitro testing except four knot-secured sutures were implanted from each lot, for each time period, using two rats. One of each knot secured sutures were implanted right and left posterior dorsal subcutis. Explanted sutures were examined visually and microscopically: it was noted that there was slight growth of tissue around the suture as a result of time,

TABLE 3

In Vitro Knot Tensile Breaking Strength Retention (BSR)

| | In Vitro Knot Tensile, lb | | | In Vitro Knot Tensile, % | | |
|---|---|---|---|---|---|---|
| Days | 60/40 PDS/PE | 100% PDS | PDS Component* | 60/40 PDS/PE | 100% PDS | PDS Component |
| 0 | 53.8 | 32.5 | 23.8 | 100 | 100 | 100 |
| 4 | 54.4 | 26 | 24.4 | 101 | 80 | 103 |
| 7 | 49.5 | 20.2 | 19.5 | 92 | 62 | 82 |
| 11 | 47.3 | 8.7 | 17.3 | 88 | 27 | 73 |
| 14 | 40.2 | 4.1 | 10.2 | 75 | 13 | 43 |
| 18 | 30.6 | 1.6 | 0.6 | 57 | 5 | 3 |
| 21 | 31.2 | 0.6 | 1.2 | 58 | 2 | 5 |

*Based on subtracting 30 lb for the UHMW PE component per the design.

not as a result of suture composition. Sutures were tested on the Instron Tensile Tester using Herrmann's loop fixture, 2"/min XH speed to obtain breaking strength.

Figure 6:
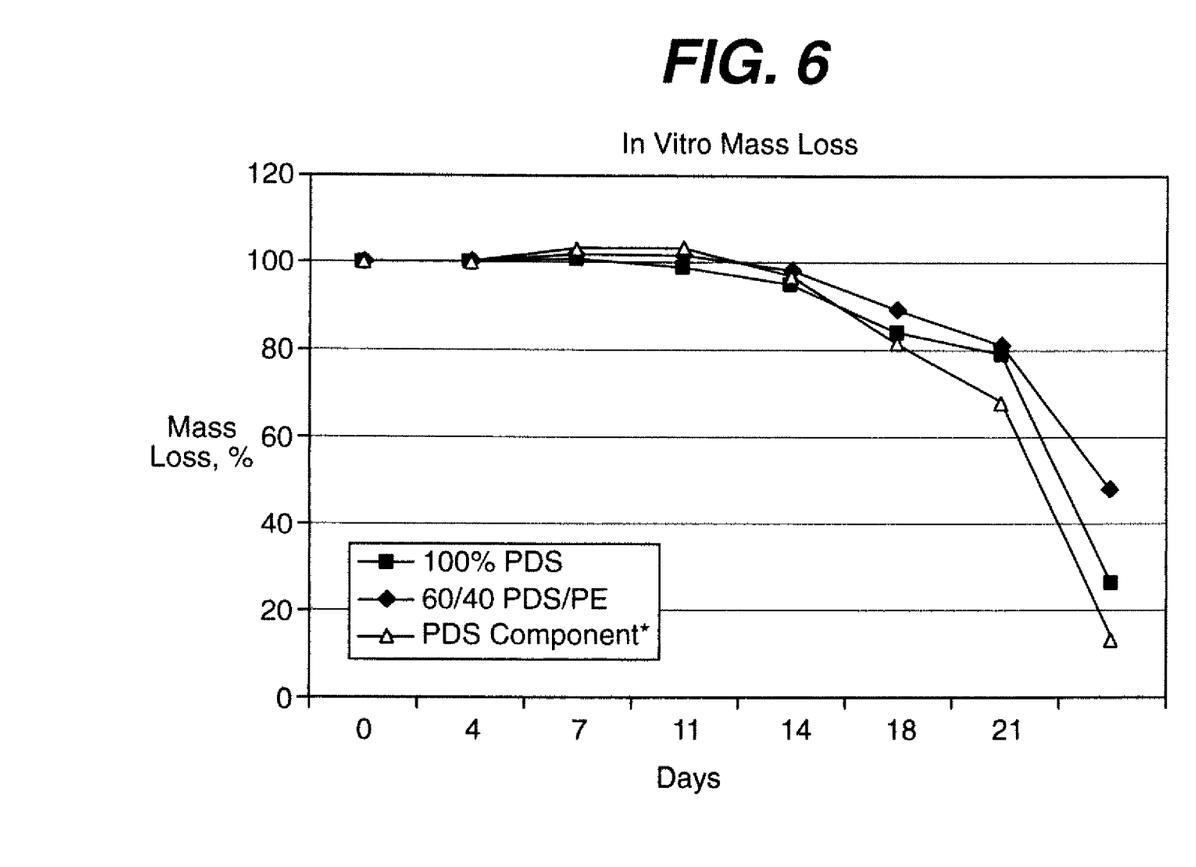
FIG. 6 is a graft of In Vitro Mass Loss % vs. Days further presenting data of Example 4

Analysis of this data is displayed in Table 5 and FIG. 6 and gave very similar results to the in vitro data. The difference between the knot strength retention for the PDS component of the composite braid from the 100% PDS is even more pronounced for in vivo implantation than for the in vitro testing. Again this is a highly desirable feature and is not anticipated.

TABLE 5

In Vivo Knot Tensile

| | Knot Tensile, lb | | | Knot Tensile, % | | |
|---|---|---|---|---|---|---|
| Days | 60/40 PDS/PE | 100% PDS | PDS Component | 60/40 PDS/PE | 100% PDS | PDS Component |
| 0 | 52.9 | 31.7 | 22.9 | 100 | 100 | 100 |
| 21 | 54.2 | 12.0 | 24.2 | 102 | 38 | 106 |
| 35 | 53.7 | 6.0 | 23.7 | 102 | 19 | 103 |
| 42 | 54.3 | 4.0 | 24.3 | 103 | 13 | 106 |
| 49 | 50.7 | 4.8 | 20.7 | 96 | 15 | 90 |
| 63 | 44.9 | 2.9 | 14.9 | 85 | 9 | 65 |

Example 5

Knot Profile Reduction

Boil Out Test

An accelerated absorption test (boil-out) in 0.05N Sodium Hydroxide solution was conducted using coated suture of Example 1 to verify whether suture knot profile was being reduced after the polydioxanone component was absorbed.

Five samples were prepared by tying loops in the suture, each having a knot consisting of five surgeon's throws. Each sample was labeled accordingly. The thickness of each knot was measured and recorded using a Mitutoyo digital gauge. The measurement was performed with the suture loop lying on the anvil and with the knot being placed between the center of the anvil and the micrometer foot. A 500 ml Pyrex bottle with 0.05N Sodium Hydroxide solution was prepared. The knots were placed into the bottle, with the bottle sealed using a tight lid. The bottle was then placed into a water bath at 90° C. for about twenty-four hours.

After twenty-four hours "boil-out", the samples were removed from the bottle and dried for one hour. The thickness of each knot was measured again. The results are exhibited in the Table 6 below.

TABLE 6

| | Knot Thickness Before Absorption, mils | Knot Thickness After Absorption, mils |
|---|---|---|
| 1 | 80.45 | 31.40 |
| 2 | 68.50 | 37.15 |
| 3 | 66.45 | 36.65 |
| 4 | 76.25 | 38.00 |
| 5 | 75.95 | 43.45 |
| Avg | 73.52 | 37.33 |
| Std | 5.84 | 4.29 |

This experiment demonstrates that the knot profile was reduced by about 50% after the bioabsorbable polydioxanone component is absorbed. The suture flattens, making the knot less palpable and thus, reducing tissue irritation.

In another experiment, an in vitro absorption test was conducted using the coated suture of Example 1.

Samples were prepared by tying loops in the suture, each having a knot consisting of six half hitch knots, alternating throw, alternating posts. Each sample was labeled accordingly. The samples were placed in phosphate buffered solution at 57° C. for a period of 26 weeks. The samples were weighed and the volume of the samples was calculated. These results were compared to Day 0 samples. The results are shown in Table 7 below.

TABLE 7

| | Day 0 | 26 week | % Reduction |
|---|---|---|---|
| Mass | 0.033 g | 0.013 g | 60% |
| Volume | 39.4 mm$^3$ | 24.8 mm$^3$ | 40% |

Example 6

In this example, an antimicrobial, Triclosan, is blended with a powdered form of a biodegradable polymer such as polydioxanone. The blending is carried out in a Brabender, Baker Perkins Blender, or a V-blender, and is generally although not necessarily done at an elevated temperature. Solvents may be added if desired to help improve the blending; the dispersing solvent is then generally removed prior to extrusion. The resulting composition is extruded using a single or twin extruder, or pelletized. Once blended, the material was re-extruded using a conventional single or twin screw extruder with a die that is capable of forming a monofilament or multifilament fiber. This fiber is either collected directly from the spinneret with no other modification, or it can be optionally post processed by annealing and drawing. Resin throughput, take-up speed and the extent of drawing dictate the diameter and degree of orientation of the fiber. The fiber is spun into a yarn.

Example 7

The absorbable multifilament yarn of Example 6 is used to make a composite suture of the present invention by following the process of Example 1 and substituting the yarn of Example 6 for the bioabsorbable yarn of Example 1.

Example 8

Bending Stiffness Test

Five suture strands 1.5 inch in length were prepared from each lot for testing. A special fixture (described below) was used with the Instron Tensile Tester (Model 4201) to measure the resistance of the force required to pull the suture through the opening in the fixture. A load cell of 500 g was used for this test. The crosshead speed was one inch per minute. The information from the test was gathered electronically.

Figure 7:
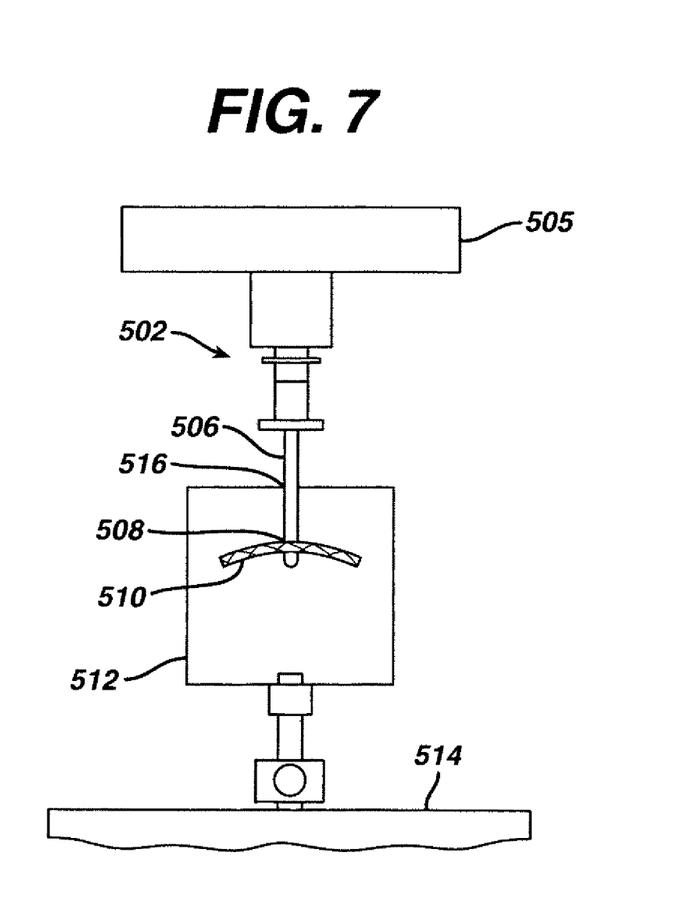
FIG. 7 is a schematic of the testing apparatus for Example 8.

The upper portion of this fixture is illustrated in FIG. 7. The fixture 502 consists of the metal rod 506 with a passage 508 at the end of the rod for threading the suture 510 through. The upper end of the rod was connected to load cell 505. The lower portion of the fixture consists of a bracket 512 attached to the machine base 514. That bracket has an opening 516 is 10 mm, which was slightly larger than the diameter of rod 506. The center of this opening 516 was lined up with the center of the metal rod.

Five samples of 1.5 inch each of the suture of Example 1 were prepared. Each sample was inserted through passage 508 in the metal rod until length of suture on each side of opening was about the same. Then, the crosshead was getting started and the suture was pulled through opening in the bracket. When the suture sample was pulled through the opening in the bracket, the resistance in grams is being recorded. Five samples were measured and the results were averaged to provide the reported values.

The results as presented in Table 8 demonstrate that the polyethylene/polydioxanone suture of the present invention had better bending stiffness than FiberWire polyethylene/an aromatic polyester suture, and had similar properties to an aromatic polyester suture.

TABLE 8

Bending Stiffness Test Results

|  | PET | Present Invention | UHMWPE/PET Stripped | UHMWPE/PET Blue |
|---|---|---|---|---|
| Average Stiffness, grams | 0.816 | 0.986 | 1.849 | 3.195 |
| St Dev | 0.148 | 0.239 | 0.601 | 0.295 |

Example 9

A patient is prepared for rotator cuff surgery in a conventional manner. The patient is anesthetized using conventional anesthesia. The pathology is identified and diagnosed arthroscopically using a conventional trocar and a conventional arthroscope. The surgeon views the site of the injury using a conventional arthroscope inserted through a cannula that is emplaced in the shoulder adjacent to the injury site. The surgeon releases any adhesions, debrides the lateral margin of the rotator cuff, immobilizes the tendon and prepares the bone bed. The surgeon locates an optimal suture anchor placement site on the 'downside' of the greater tuberosity of the patient's humeral head and drills a bone hore hole for anchor emplacement in the following manner. A drill guide is inserted through the trocar. A drill bit is placed through the drill guide and the bore hole is drilled for the suture anchor. A conventional suture anchor such as the suture anchor illustrated in FIG. 3 having a suture of the present invention mounted thereto is inserted and emplaced in the bore hole engaging the cancellous bone below the bone cortex. Surgical needles attached to the ends of the suture are used to penetrate the soft tissue (i.e., tendon) such that the soft tissue is approximated to the surface of the bone. The suture is then knotted in a conventional manner using a conventional surgical knot. The needles are then cut from the suture and the procedure is then complete and the patient's external fascia and skin are approximated in a conventional manner by suturing or using surgical tape or surgical glues.

The sutures of the present invention have many advantages. The advantages include maximized suture mass reduction over time, reduced knot profile over time, improved BSR profile, and high tensile strength, and improved handling characteristics.

Although this invention has been shown and described with respect to detailed embodiments thereof, it will be understood by those skilled in the art that various changes in form and detail thereof may be made without departing from the spirit and scope of the claimed invention.

The invention claimed is:

1. A combination of a surgical suture and a suture anchor, comprising:
   I) a suture anchor, said anchor comprising an anchor body and a suture mounting passage therein; and,
   II) a surgical suture, said suture comprising,
      an inner core comprising at least a first yarn comprised of at least one fiber, said fiber comprising a bioabsorbable polymer; and,
      an outer braided sheath comprising a second yarn comprised of at least one nonabsorbable fiber and a third yarn comprising at least one bioabsorbable fiber, wherein the second and third yarns are in intertwining contact,
   wherein the suture is mounted to the suture mounting opening of the suture anchor, and wherein the suture comprises about 55 wt. % to about 70 wt. % of bioabsorbable polymer.

2. The combination of claim 1, wherein the bioabsorbable first and bioabsorbable third yarns comprise a polymer prepared from lactone monomers selected from the group consisting of p-dioxanone, ε-caprolactone, glycolide, L(−)-lactide, D(+)-lactide, meso-lactide, trimethylene carbonate, and combinations thereof.

3. The combination of claim 2, wherein the bioabsorbable first and third yarns comprise polydioxanone.

4. The combination of claim 3 wherein the bioabsorbable first and third yarns comprises a filament having a denier greater than 3 denier per filament.

5. The combination of claim 3 wherein the bioabsorbable first and third yarns comprises a filament having a denier greater than 12 denier per filament without substantial adverse effect to suture handling and stiffness when compared to the commercially available sutures prepared from ultra high molecular weight polyethylene/PET.

6. The combination of claim 3 wherein the bioabsorbable first and third yarns comprises a filament having a denier greater than 12 denier per filament without substantial adverse effect to suture handling and stiffness when compared to the sutures prepared from polyethylene terephthalate with a denier per filament less than 3.

7. The combination of claim 1, wherein the nonabsorbable fiber comprises ultra high molecular weight polyethylene.

8. The combination of claim 1, wherein the bioabsorbable first and third yarns comprise a pharmaceutical composition.

9. The combination of claim 8 wherein the first and third yarns comprise a pharmaceutical composition selected from the group consisting of analgesics, antibiotics, anti-inflammatories, and pain killers.

10. The combination of claim 1 wherein the second yarn comprises an ultra high molecular weight polyethylene having a weight average molecular weight of about 500,000 to about 5,000,000 g/mole.

11. The combination of claim 1, additionally comprising a coating on the suture.

12. The combination of claim 1 additionally comprising a surgical needle mounted to one end.

* * * * *